United States Patent [19]

Sternberg

[11] 4,340,482
[45] Jul. 20, 1982

[54] PROCESS FOR GRAFTING AMINO ACID MOLECULES ONTO PREFORMED POLYMER SURFACES AND PRODUCTS PREPARED THEREBY

[75] Inventor: Shmuel Sternberg, Lexington, Mass.

[73] Assignee: Millipore Corporation, Bedford, Mass.

[21] Appl. No.: 136,908

[22] Filed: Apr. 3, 1980

Related U.S. Application Data

[63] Continuation of Ser. No. 879,746, Feb. 21, 1978, abandoned.

[51] Int. Cl.³ .............................................. B01D 31/00
[52] U.S. Cl. .................................. 210/500.2; 427/245
[58] Field of Search .......... 264/22; 427/316, 244–246; 526/18, 17, 49; 428/304; 210/500 M, 22, 23 H, 23 F, 321 R, 321 A, 321 B; 521/27; 195/68, 63, DIG. 11

[56] References Cited

U.S. PATENT DOCUMENTS

| 2,979,490 | 4/1961 | West | 526/18 |
| 3,615,024 | 10/1971 | Michaels | 210/500 M X |
| 3,621,085 | 11/1971 | Ichikawa | 526/17 X |
| 3,632,387 | 1/1972 | Sutherland | 427/316 X |
| 3,652,761 | 3/1972 | Weetall | 195/DIG. 11 |
| 3,750,735 | 8/1973 | Chiang et al. | 210/500 M X |
| 4,188,354 | 2/1980 | Munari et al. | 264/22 |

FOREIGN PATENT DOCUMENTS 814560  6/1959  United Kingdom .................. 521/27

Primary Examiner—Frank A. Spear, Jr.
Attorney, Agent, or Firm—Paul J. Cook; David Prashker

[57] ABSTRACT

Amino acid subject to attack by free radicals can be grafted onto the surface of a preformed polymer by treating the surface with a highly basic solution of the molecules to be grafted. Using this method, a preformed poly(vinylidene fluoride) surface can be rendered hydrophilic by subjecting the surface to a highly basic solution of glycine.

13 Claims, No Drawings

PROCESS FOR GRAFTING AMINO ACID MOLECULES ONTO PREFORMED POLYMER SURFACES AND PRODUCTS PREPARED THEREBY

This is a continuation of application Ser. No. 879,746, filed Feb. 21, 1978, now abandoned.

BACKGROUND OF THE INVENTION

1. Field of the Invention

This invention relates to a method of grafting molecules onto preformed polymer surfaces.

2. Description of the Prior Art

It is often considered desirable to be able to change the surface characteristics of a polymer surface without affecting the other advantageous physical and chemical characteristics of the polymer. Numerous preformed polymer surfaces, such as those of molded or shaped polymers or of polymer coatings, are dependent upon their surface characteristics for effective utilization in their contemplated applications. Microporous membranes and skinned or molecular filtration membranes are examples of preformed polymers whose effectiveness depends to a great extent upon their surface characteristics.

Microporous membranes are thin sheets having uniform continuous porous structures which function as absolute screens, retaining on their surfaces all bacteria, viruses, macromolecules or particles larger than the pore diameter. Such membranes can be effectively used as filters for cold sterilization in the pharmaceutical and food processing industries.

Skinned membranes consist of thin polymeric films supported on a highly porous structure. Since skinned membranes retain most molecules above a nominal molecular weight limit, these membranes may suitably be used as molecular filters for desalination, concentration, purification of viruses, macromolecules and small molecules, and other similar applications.

To be useful in these applications, microporous and skinned membranes are desirably made from materials which are chemically and biologically inert and exhibit good mechanical properties and structural stability. Fluorocarbon polymers, such as polyvinylidene fluoride, have been found to be particularly suitable.

Hydrophilic membranes which are readily wet by an aqueous solution allow the liquid to flow therethrough, but do not permit the flow of gas, micro-organisms and micron-size particles when wet. Hydrophobic membranes, by contrast, which are not wet by an aqueous solution and do not permit its passage therethrough, allow gas to pass readily while maintaining their effectiveness to filter micro-organisms and micron-size particles. Both hydrophilic and hydrophobic membranes can be used, for example, in the sterilization of liquids being administered intravenously. A hydrophilic membrane placed in the path of the liquid would filter gas and micro-organisms harmful to the patient. A hydrophobic membrane could be employed to vent the filtered gas to the atmosphere without loss of any of the aqueous liquid.

The fluorocarbon polymers such as poly(vinylidene fluoride) which are particularly suitable membrane materials are generally hydrophobic, and therefore, cannot be used in those applications requiring a hydrophilic surface.

Prior to the present invention, a hydrophobic membrane could be treated with a solution of a water-insoluble wetting agent to render it hydrophilic. It has been found, however, that steam sterilization of or passage of water through membranes that had been so treated resulted in the partial loss of their hydrophilic character. Therefore, a method was needed which would render the polymer surface more stably hydrophilic.

It is known that fluorocarbon polymers can be treated with medium-to-strong bases to remove hydrogen fluoride from the polymer chain and crosslink the polymer. See, e.g., Smith, "The Chemistry of Vulcanization of 'Viton' A Fluorocarbon Elastomer", Rubber World, Vol. 142, pp. 102–107 (1960); Paciorek et al., "Mechanism of Amine Crosslinking of Fluoroelastomers. I. Solution Studies", J. Polymer Sci., Vol. 65, pp. 405–413 (1960); Mark, Encyclopedia of Polymer Science and Technology, Vol. 14, pp. 612–613 (1971). It is observed by Dwight et al., "Fluoropolymer Surface Studies", J. Colloid Sci., Vol. 47, No. 3, pp. 650–660 (1974) that etching of the surface of a fluorocarbon polymer with a solution of sodium in ammonia removes most of the fluorine and results in a surface which exhibits the characteristics of an unsaturated oxidized hydrocarbon and is relatively unstable.

In U.S. Pat. No. 2,972,586 films of hydrophobic materials such as polyvinyl chloride and copolymers of vinyl chloride and vinylidene chloride are made hydrophilic by the introduction of ionic groups into the film. The reaction involves replacement of halogen atoms in the film forming material by quaternary ammonium or guanidinium groups, of tertiary sulfonium or sulfonic groups.

In U.S. Pat. No. 3,617,344 polymer surfaces are rendered nonthrombogenic by heparin chemically combined with quaternary ammonium groups which are chemically bonded to the polymer surfaces. In one embodiment, a polymer, such as polytetrafluoroethylene, is provided with tertiary amine groups on its surface by radiation grafting of a tertiary amine to the surface, and the chemically bonded tertiary amine groups are then quaternized with a quaternizing agent. The quaternary ammonium groups are then heparinized.

In U.S. Pat. Nos. 3,380,848, 3,401,049, 3,494,862, 3,698,931, 3,880,580, 2,929,800, and 3,940,377 various methods are disclosed in which polymeric surfaces are treated with solutions of silver salts and polymerizable monomers so that silver or silver oxide is deposited on the surface in order to catalyze the grafting and polymerization of the monomer onto the surface.

Although the prior art discloses processes for treating a polymer with either a medium-to-strong base or a substance to be reacted with the polymer, none of these processes discloses a process for subjecting a polymer surface to the action of both the base and the reactant substance for the purpose of grafting the reactant substance onto the surface of the polymer.

SUMMARY OF THE INVENTION

In accordance with the present invention, the surface properties of a preformed polymer can be modified without affecting the other physical and chemical properties of the polymer. The present process comprises treating the surface of a preformed polymer, such as poly(vinylidene fluoride), with a highly basic reagent solution containing molecules having the characteristics desired to be conveyed to the polymer surface. Under these reaction conditions the molecules become grafted onto the polymer surface so that the surface exhibits the properties of the molecule rather than those of the polymer.

Although the reaction mechanism is not known, and applicants do not wish to be bound to any theory thereof, it is believed, for example, that when the surface of a polymer such as poly(vinylidene fluoride) is attacked by the strong base, fluorine and hydrogen are eliminated from the chain and active sites are created on the surface. At this point the reaction becomes statistical in nature so that reactive sites combine with whatever species they encounter first, without any particular affinity for any species. The reactive sites can combine to form double bonds, attack another part of the same chain or another chain, or graft to a molecule that can be attacked by free radicals.

DESCRIPTION OF THE PREFERRED EMBODIMENTS

Fluorocarbon polymers and particularly poly(vinylidene fluoride) exhibit chemical and physical properties which render them highly suitable for use in the manufacture of microporous and molecular filtration membranes. A significant drawback to the universal application of membranes made from such fluorocarbon polymers is the hydrophobic nature of their surfaces.

It has been found that the process of the present invention can be utilized to provide a hydrophilic surface on the polymer which is more resistant to degradation than heretofore possible.

The reagent solution should contain a strong base to attack the polymer surface. The strong base used in the solution can be the substance to be grafted to the polymer surface, or another substance used for its ability to attack the polymer surface, or both. Primary amines are very basic substances which attack poly(vinylidene fluoride) and other fluorocarbon polymers. Another strong base such as sodium hydroxide can be added to enhance their attack on the polymer surface. If a strongly basic solution, e.g. pH 13-14, of the molecules to be grafted could be prepared without the addition of another strong base, it is believed that the polymer surface would be sufficiently attacked. Since it was desired to graft molecules to preformed poly(vinylidene fluoride) surfaces which would render the surfaces hydrophilic in nature, glycine was chosen to be grafted. The reaction mixture found to be most effective contained glycine, sodium hydroxide and water. By varying the ratio of the reactants, the reaction time required for a given graft content can be controlled. At high pH and at high temperature near the boiling point of the reaction mixture, glycine in the form of the glycinate ion is grafted onto the surface of poly(vinylidene fluoride). The reaction will proceed at a slower rate with lower pH and/or lower temperature. The most satisfactory results, however, are obtained in a shorter period of time by reacting at both high temperature and high pH.

The molecules that can be grafted to the polymer surface are not limited to molecules like glycine or amines in general. Since it is theorized that the reaction becomes statistical in nature after the formation of free radicals on the polymer surface, any molecule of any size that can be attacked by free radicals can be grafted to the polymer surface. Suitable molecules which can be grafted include sulfamic acid, p-aminobenzoic acid, diethylenetriamine, lactic acid, sulfanilic acid, and hydroxylamine. Since the reaction occurs under highly basic conditions, these compounds exist as salts, such as sodium sulfamate, p-aminobenzoate, sodium sulfanilate, etc. Selection of a molecule which is subject to free radical attack to graft onto the polymer surface will depend on the desired function and ultimate end use of the polymer surface. For example, as described above, glycine was selected to enhance the wettability of the polymer surface. Under strong caustic conditions the glycine was in the form of sodium glycinate so that the glycinate ion could not react with the reactive sites on the polymer chain. However, if ethanolamine were selected as the molecule, a hydrophilic surface would not be obtained after the reaction because the hydroxyl group would not be protected from the reaction and would be attacked by a free radical and grafted onto the polymer chain as well. Although polymers and copolymers of vinylidene are the preferred polymer surfaces, polymers and copolymers of vinylidene chloride, such as vinylidene chloride-acrylonitrile copolymer, can be employed in the present process.

The preformed polymer surface onto which molecules may be grafted in accordance with the present process need not be a microporous or molecular filtration membrane. The solid preformed polymer surface can be in any desired shape. By using the present process, surface can be designed, for example, for enzyme binding, special packings for affinity chromatography, covalent binding of antigens or antibodies, and the like. Moreover, once the desired molecule has been grafted onto a particular surface, the molecule can be further reacted in order to modify its characteristics. For example, glycine grafted onto a poly(vinylidene fluoride) surface could be reacted to bind a bioreactant to the glycine.

Thus, in accordance with the present invention, the destructive reaction of a strong base attacking a polymer surface, which would normally be avoided by all users of the polymer, has been utilized beneficially to produce reactive sites on the polymer surface onto which a functional molecule can be grafted to produce a predetermined surface characteristic, without affecting the physical and chemical properties of the backbone polymer. The process could also be used, for example, to modify the polymer surface so as to change its printing characteristics. It is also significant that none of the other advantageous physical and chemical properties of poly(vinylidene fluoride) are affected during grafting, with the exception that in a porous polymer surface percent elongation to break is reduced due to the porous nature of the surface.

A more complete appreciation of the invention will be realized by reference to the following specific examples relating to specific compositions and processes for preparing specific products. The following examples are not intended to limit the invention disclosed herein except to the extent that limitations are specifically stated or to the extent to which limitations appear in the appended claims.

EXAMPLE 1

A buffer solution of 1 percent borate/carbonate at a pH of 9.80 and a 0.1 M buffer solution of phosphate at a pH of 12.00 were prepared. Into 200 milliliters of each of these buffers was dissolved 50 grams of glycine. The pH of the borate/carbonate/glycine solution was adjusted to 9.00 by adding 230 milliliters of a 50 weight percent solution of sodium hydroxide. This resulted in a 21.8 percent solution of glycine. The pH of the phosphate/glycine solution was then adjusted to 12.00 by adding 265 milliliters of the 50 weight percent sodium hydroxide solution resulting in an 18.9 percent glycine solution.

Microporous membranes of poly(vinylidene fluoride) were treated with the two glycine solution at 95° C. for 1, 2, 3 and 19 hours and then tested with solutions of methanol in water of various concentrations to determine their resulting wettability. The values set forth in Table I below are given as weight percent methanol in water:

TABLE I

| Time of Treatment at 95° C. (hr.) | 21.8% Glycine at pH 9.00 | 18.9% Glycine at pH 12.00 |
|---|---|---|
| 1 | 35 | 35 |
| 2 | 35 | 30 |
| 3 | 35 | 25 |
| 19 | 30 | 0 |

Untreated poly(vinylidene fluoride) membranes are wetted with alcohol solutions of 40 percent and higher. Referring to Table I, it can be seen that increasing the pH from 9 to 12 increases the rate and amount of reaction. The only completely wettable sample obtained after 19 hours of treatment with the 18.9 percent glycine solution was found to be brown and unacceptably brittle.

EXAMPLE 2

A 41.2 percent solution of glycine having a pH of 13.5 was prepared by adding 35 grams of glycine to 50 milliliters of a 6 N solution of sodium hydroxide and heating to boiling. At a boiling temperature of 112° C. all of the glycine had dissolved in the caustic solution.

Six pieces of poly(vinylidene fluoride) membrane were wet with methanol and extracted in hot water for 10 minutes. The water-wet membranes were then placed in the boiling glycine solution for 0.25, 1, 2, 3, 6 and 7.5 hours and tested for wettability. The percent of methanol in water required to completely wet each of the treated membranes is listed in Table II below:

TABLE II

| Time of Treatment at 112° C. (hr.) | 41.2% Glycine at pH 13.5–14.0 |
|---|---|
| 0.25 | 35 |
| 1 | 35 |
| 2 | 30 |
| 3 | 25 |
| 6 | 10 |
| 7.5 | 0 |

As can be seen from Table II, as the pH and temperature increased over those of Example 1, the wettability increased more rapidly and a completely wettable sample which was light tan in color was obtained after 7.5 hours of reaction. The completely wettable sample retained acceptable crease resistance.

EXAMPLE 3

Using a glycine solution similar to that of Example 2 but prepared from a 50 percent solution of sodium hydroxide, it was found that the reaction rate was greatly increased, but that the poly(vinylidene fluoride) membrane became very brittle before becoming completely wettable. Thus it appeared that a high caustic concentration was needed for a fast reaction, but a very high glycine concentration was needed to get wettability before losing acceptable flexibility and color.

A 50 percent solution of glycine was then prepared by adding 70 grams of glycine to 50 milliliters of a 50 weight percent solution of sodium hydroxide and heating to boiling at 122° C. Two pieces of poly(vinylidene fluoride) membrane were treated with the solution for 10 and 45 minutes. The percent of methanol in water needed to completely wet each membrane is set forth in Table III below:

TABLE III

| Time of Treatment at 122° C. (min.) | 50% Glycine Solution |
|---|---|
| 10 | 25 |
| 45 | 5 |

The two membranes retained the necessary flexibility and strength indicating that the reaction occurred primarily on the polymer surface.

EXAMPLE 4

A solution of 57 percent glycine, 23 percent sodium hydroxide, and 20 percent water was heated to 120° C. Poly(vinylidene fluoride) membranes were treated for 5, 15 and 75 minutes in the hot glycine solution. The wettability of the treated membranes determined by the percent methanol in water required to completely wet the membranes is set forth in Table IV below:

TABLE IV

| Time of Treatment at 120° C. (min.) | 57% Glycine Solution |
|---|---|
| 5 | 35 |
| 15 | 30 |
| 75 | 0 |

After 75 minutes of reaction at 120° C., a flexible, completely wettable membrane was obtained which was light tan in color. The properties of the membrane were not adversely affected by the treatment.

EXAMPLE 5

A 50 percent glycine solution was prepared by mixing 500 grams of glycine with 250 grams of sodium hydroxide and 250 grams of water. The solution was heated to boiling at 122° C. and then reduced to just below boiling at 118°–120° C. Samples of poly(vinylidene fluoride) membrane were treated with the glycine solution for 5, 35 and 65 minutes. The percent of methanol in water required to set each sample is listed in Table V below:

TABLE V

| Time of Treatment at 120° C. (min.) | 50% Glycine Solution |
|---|---|
| 5 | 30 |
| 35 | 5 |
| 65 | 0 |

The sample treated for 5 minutes did not wet after it was neutralized with dilute sulfuric acid, washed, and dried. The sample was reset with methanol, extracted with water, soaked in monobasic sodium phosphate solution and it chen wet as indicated in Table V. The sample treated for 35 minutes wet after extraction with water and drying and wet slowly after neutralization with the dilute acid solution. The samples treated for 65 minutes completely wet regardless of the post treatment.

To the glycine solution were added 125 grams of sodium hydroxide and 250 grams of glycine to produce a solution of 53.6 percent glycine, 28.6 percent sodium hydroxide, and 17.8 percent water. The solution was then brought to boiling, left for about 16 hours at 105° C., and again brought back to boiling at 132° C. A poly(vinylidene fluoride) membrane was treated with the solution for 15 minutes at 132° C., washed in very hot running water for about 10 minutes and dried. The resulting membrane was instantly wettable. The same sample was neutralized in dilute sulfuric acid solution for 10 minutes and was still found to be instantly wettable.

Another sample of poly(vinylidene fluoride) membrane was treated with the 53.6 percent glycine solution for 7 minutes at 132° C., washed in very hot running water for about 10 minutes, and dried. The resulting surface was quickly wettable, although not quite as fast as the previous sample. This sample was then neutralized in dilute sulfuric acid and then found to be instantly wettable.

A further sample was treated with the same glycine solution at 132° C. for 3 minutes, rinsed for about 10 minutes in hot running water and dried. The sample did not wet completely.

Another poly(vinylidene fluoride) sample was treated with the same solution for 5 minutes at 133° C., rinsed for 10 minutes in hot running water, and dried. The surface was instantly wettable. The sample was then neutralized in dilute sulfuric acid solution for 10 minutes, and found to be instantly wettable.

The glycine solution was left for about 16 hours at 122° C. A sample of poly(vinylidene fluoride) membrane was then treated with the solution for 5 minutes at 122° C., rinsed with hot running water for 10 minutes, and dried. The surface of the resulting membrane was not very wettable. To verify that this lack of wettability was due to the lower temperature employed, a similar sample was treated with the solution at 138° C. for 5 minutes, rinsed with hot running water for 10 minutes, and dried. the surface was instantly wet. The sample was then neutralized for 30 minutes in dilute sulfuric acid solution and found to wet instantly.

From the above series of experiments, the best results were obtained at 132° C., just below the boiling point of the reagent mixture, with a dilute acid wash to neutralize the remaining caustic. The resulting materials were cream to light tan in color, flexible, and water-wettable.

EXAMPLE 6

Five pieces of poly(vinylidene fluoride) membrane were soaked in methanol. The methanol was then extracted with water, and the water was then exchanged for glycine solution by treating the pieces with a solution prepared from 750 grams of glycine, 375 grams of sodium hydroxide, and 250 grams of water for 5 minutes at 96° C. The pieces were then reacted with the glycine solution used in the majority of the experiments of Example 5 above at 137° C. for 5, 10, 20, 40 and 80 minutes. The treated pieces were then water extracted for 15 minutes, reacted in dilute sulfuric acid solution for 5 minutes, rinsed with water for 10 minutes, and then dried on the ferrotype plate at a dial setting of 200.

For comparison, a sixth piece of membrane was annealed at 135° C. in a vacuum oven for 5 minutes. The six samples and an unannealed control were the evaluated on the prosimeter. The data obtained is set forth in Table VI below:

TABLE VI

| Treatment | 75% Wet/Dry Flow Pressure (psi) | Water Flow Rate (cm/sec) | $H_2O$ Bubble Point (psi) |
| --- | --- | --- | --- |
| None | 59.3 | 33 | 29.9 |
| 135° C. - 5 min | 55.3 | 26 | 28.4 |
| NaGly - 5 min $H_2SO_4$ wash | 71.7 | 39 | 14.6 |
| NaGly - 10 min $H_2SO_4$ wash | 73.1 | 38 | 46.1 |
| NaGly - 20 min $H_2SO_4$ wash | 72.9 | 38 | 28.0 |
| NaGly - 40 min $H_2SO_4$ wash | 75.9 | 40 | 32.4 |
| NaGly - 80 min $H_2SO_4$ wash | 82.0 | 31 | 44.0 |

Since a single piece of each membrane was measured, the bubble point values may depend more on sample uniformity than typical pore size.

EXAMPLE 7

Several pieces of poly(vinylidene fluoride) were soaked in methanol and then extracted in running water for 10 minutes. The pieces were placed in Milli-Q water to soak over a weekend and then soaked in the first glycine solution employed in Example 6 above for 5 minutes at 96° C. The pieces were then reacted in the second glycine solution of Example 6 at 137° C. for 5, 10, 20, 40 and 80 minutes. Then, the treated pieces were extracted for 15 minutes in hot running water and soaked for 20 hours in Milli-Q water. Each piece was then cut into two disks. One of the disks was soaked in a 0.1 N sodium hydroxide solution for 30 minutes and the other was soaked in a 1.0 M hydrochloric acid solution for 30 minutes. The treated disks were then exchanged in Milli-Q water for 30 minutes and dried at 60° C. for 60 minutes. Then, each disk was weighed and tested for initial wettability. The disks were then subjected to dry heat in a vacuum oven at 135° C. for 0.5, 1.5, 2, 4, 8 and 16 hours and tested for wettability. The percent methanol in water required to wet each disk is set forth in Table VII below:

TABLE VII

| Surface Treatment | Dry Heat at 135° C. (hrs) | | | | | | |
| --- | --- | --- | --- | --- | --- | --- | --- |
| | 0 | 0.5 | 1.5 | 2 | 4 | 8 | 16 |
| NaGly - 5 min | | | | | | | |
| HCl wash | 0 | 0 | 15 | 15 | 15 | 20 | |
| NaOH wash | 0 | 0 | 0 | 0 | 5 | 15 | |
| NaGly - 10 min | | | | | | | |
| HCl wash | 0 | 0 | 15 | 15 | 15 | 20 | |
| NaOH wash | 0 | 0 | 10 | 20 | 30 | 35 | |
| NaGly - 20 min | | | | | | | |
| HCl wash | 0 | 0 | 20 | 15 | 15 | 20 | |
| NaOH wash | 0 | 0 | 10 | 15 | 30 | 25 | 35 |
| NaGly - 40 min | | | | | | | |
| HCl wash | 0 | 0 | 20 | 20 | 20 | 25 | |
| NaOH wash | 0 | 0 | 10 | 15 | 30 | 35 | |
| NaGly - 80 min | | | | | | | |
| HCl wash | 0 | 0 | 10 | 10 | 15 | 20 | |
| NaOH wash | 0 | 0 | 0 | 0 | 5 | 30 | |

Referring to Table VII, it can be seen that some loss of wettability occurs when the membranes are subjected to dry heating at 135° C.

What is claimed is:

1. A preformed microporous polymeric article having a surface onto which molecules of an amino acid have been grafted to produce an altered surface characteristic without altering substantially the subsurface physical and chemical properties of the polymer, wherein the polymer in predominantly a fluorocarbon polymer having a polyvinyl carbon chain to which alternating hydrogen and fluorine atoms are attached, and wherein the amine residue of the amino acid is reacted with and grafted to reactive sites on the polymeric surface.

2. An article according to claim 1 wherein said article is a microporous or skinned membrane having amino acid molecules grafted substantially only to the surfaces thereof, the grafted membrane retaining substantially the strength and flexibility of the membrane prior to grafting.

3. An article according to claims 1 or 2 wherein said polymer is predominately poly(vinylidene fluoride).

4. The article of claims 1 or 2 where the amino acid is glycine.

5. The article of claim 3 wherein the amino acid is glycine.

6. A process for grafting molecules of an amino acid onto a preformed microporous surface of a polymeric article to produce thereon an altered surface characteristic without substantially affecting the subsurface chemical and physical properties of the article comprising treating the surface with a basic solution of the amino acid to be grafted, the polymers comprising predominantly fluorocarbon polymers having polyvinyl carbon chains to which alternating hydrogen and fluorine atoms are attached, and wherein the amine residue of the amino acid is active with the reactive sites on the polymer surface the amount of hydroxide base in said solution being sufficient in the presence of said amino acid to create said reactive sites on said polymer surface without substantially affecting subsurface polymers.

7. A process according to claim 6 wherein the amount of hydroxide base in said solution is not substantially in excess of that necessary to react with said amino acids to form salts therewith.

8. A process according to claim 6 wherein said solution has a pH less than 14.

9. A process according to claim 6 wherein said solution is substantially a solution of salts of amino acids formed by reacting the amino acids with alkali metal hydroxide, the amount of a alkali metal hydroxide used being not substantially in excess of the amount required to react with the amino acid to form salts therewith, the temperature of said solution being above ambient up to its boiling temperature.

10. A process according to any one of claims 6, 8, or 9 wherein said amino acid is glycine.

11. A process according to any one of claims 6, 8, 7 or 9 wherein said solution is aqueous and said article is microporous, said microporous article having a liquid miscible with water in its pores prior to treatment with said solution.

12. A process according to any one of claims 6, 8, or 9 wherein said polymer is predominately microporous polyvinylidene fluoride.

13. The process according to claims 6, 8 or 9 wherein the polymer is predominately microporous polyvinylidene fluoride and the amino acid is glycine.

* * * * *